United States Patent [19]

Stroppolo et al.

[11] Patent Number: 5,767,161
[45] Date of Patent: Jun. 16, 1998

[54] PHARMACEUTICAL COMPOSITIONS FOR TOPICAL USE CONTAINING (S)-2-(4-ISOBUTYLPHENYL) PROPINONIC ACID

[75] Inventors: Federico Stroppolo, Pregassona, Switzerland; Daniele Bonadeo, Varese, Italy; Alberto Riccardi, Caronno Varesino, Italy; Annibale Gazzaniga, deceased, late of Rescaldina, Italy, by Cisella Adele Marabelli Gazzaniga, Giovanni Battista Gazzaniga, legal representative; Paola Maria Gazzaniga, legal representative, Busto Arssizio, Italy

[73] Assignee: Zambon Group S.P.A., Milan, Italy

[21] Appl. No.: 648,014

[22] PCT Filed: Dec. 7, 1994

[86] PCT No.: PCT/EP94/04066

§ 371 Date: May 30, 1996

§ 102(e) Date: May 30, 1996

[87] PCT Pub. No.: WO95/16445

PCT Pub. Date: Jun. 22, 1995

[30] Foreign Application Priority Data

Dec. 16, 1993 [IT] Italy ................... MI93A2634

[51] Int. Cl.$^6$ ................... A61K 31/19
[52] U.S. Cl. ................... 514/570
[58] Field of Search ................... 514/570

[56] References Cited

U.S. PATENT DOCUMENTS

| 3,749,773 | 7/1973 | Ninger . |
| 4,282,216 | 8/1981 | Rovee et al. . |
| 4,954,487 | 9/1990 | Cooper et al. ........... 514/159 |
| 5,093,133 | 3/1992 | Wisniewski et al. . |

FOREIGN PATENT DOCUMENTS 2202741  10/1988  United Kingdom .

Primary Examiner—William R. A. Jarvis
Attorney, Agent, or Firm—Watson Cole Stevens Davis, P.L.L.C.

[57] ABSTRACT

A pharmacuetical composition in the form of cream, foam or stick containng 2.5–10% by weight (S)-2-(4-isobutylphenyl) propionic acid, 20–30% by weight and ethanol and 5–50% by weight propylene glycol, the ratio of ethanol to propylene glycol being 0.6–1 to 4:1.

3 Claims, No Drawings

PHARMACEUTICAL COMPOSITIONS FOR TOPICAL USE CONTAINING (S)-2-(4-ISOBUTYLPHENYL) PROPINONIC ACID

This application is a 371 of PCT/EP94/04066 filed Dec. 7, 1994.

The present invention relates to a pharmaceutical composition for topical use and, more particularly, it relates to a pharmaceutical composition for topical use containing (S)-2-(4-isobutylphenyl)propionic acid.

The compound 2-(4-isobutylphenyl)propionic acid, which will be indicated herein after with its international nonproprietary name Ibuprofen, is a known nonsteroidal anti-inflammatory drug (Merck Index XI Ed., no. 4812, page 476) used in therapy for its analgesic, antipyretic and anti-inflammatory activity.

Very recently, it has been described in literature that Ibuprofen has also a strong antifungal activity (Sanyal et al., Letters in Applied Microbiology, 1993, 17, 109–111). Notwithstanding for years Ibuprofen has been used in therapy in racemic form, for some time it has been known that the active enantiomer is the one having (S) configuration, herein after referred to as (S)-Ibuprofen.

In literature, several topical pharmaceutical compositions containing Ibuprofen are known. As an example we can cite: the analgesic compositions in the form of an oil-in-water emulsion described in the European patent application no. 499399 (American Home Products Corporation) which contain high concentrations of Ibuprofen in solid crystalline form, the compositions described in the British patent application no. 2236250 (The Mentholatum Company Limited) based on solutions of Ibuprofen in benzyl alcohol, the hydroalcoholic gel with pH 3.5–6.0 described in the European patent application no. 439344 (McNeil-PPC Inc.), the gel described in the Japanese patent application no. 60/185712 (Kyushin Pharm. K. K.). Some of these compositions provide for the use of ethanol or propylene glycol or mixtures thereof as solvent systems but always in the presence of one or more further components which are essential for achieving an increase in the cutaneous permeation of Ibuprofen, such as for example triethanolamine [Chemical Abstract, vol. 117, No. 239720 (1992)] and benzyl alcohol (the above cited British patent application no. 2236250).

It is evident that the formulation of (S)-Ibuprofen in topical dosage forms can be therapeutically very useful for the treatment of diseases such as backache, reumatic and muscular pain, sprains, strains and neuralgia or for the treatment of localized mycoses.

However, the formulation of (S)-Ibuprofen in topical dosage forms shows remarkable problems due to the different characteristics of the enantiomer with respect to the racemic mixture.

The International patent application no. WO 92/20334 (The Boots Company PLC) describes pharmaceutical compositions for oral, rectal or topical administration containing (S)-Ibuprofen sodium salt as active ingredient. In the above patent application it is reported that, the pharmaceutical composition being the same, the substitution of (S)-Ibuprofen sodium salt with the free acid, that is with (S)-Ibuprofen, does not give acceptable results.

We have now surprisingly found that (S)-Ibuprofen can be formulated in a topical pharmaceutical composition containing ethanol and propylene glycol in a ratio from 0.6:1 to 4:1, so obtaining topical compositions which are suitable from a pharmaceutical point of view, and, in addition, allow to achieve an increased cutaneous permeation of the active ingredient with respect to those obtained by known topical pharmaceutical compositions containing an equivalent or higher amount of Ibuprofen.

Therefore, object of the present invention is a pharmaceutical composition for topical use containing 2.5–10% by weight of (S)-2-(4-isobutylphenyl)propionic acid in admixture with a suitable pharmaceutically acceptable carrier characterized by the presence of 20–30% by weight of ethanol and 5–50% by weight of propylene glycol so that the weight ratio ethanol:propylene glycol is between 0.6:1 and 4:1.

In the pharmaceutical composition object of the present invention the remaining up to 100% by weight is represented by excipients such as lipophilic substances, surfactants, gelling substances, solvents, structuring agents, preserving agents, colouring agents, opacifiers, perfumes, buffers, chelating agents and anti-oxidants, commonly used for the preparation of topical pharmaceutical dosage forms. The pharmaceutical composition object of the present invention allows to achieve high levels of (S)-Ibuprofen cutaneous permeation and it is particularly useful for the formulation of (S)-Ibuprofen in topical pharmaceutical dosage forms such as creams, gels, foams and sticks.

Therefore, the pharmaceutical compositions object of the present invention can be used in therapy for the treatment of diseases such as backache, reumatic and muscular pain, sprains, strains and neuralgia or for the treatment of localized mycoses.

Preferably, the pharmaceutical compositions object of the present invention contain an amount of (S)-Ibuprofen corresponding to 5% by weight.

The weight ratio ethanol:propylene glycol is preferably from 0.6:1 to 2:1.

The pharmaceutical composition object of the present invention allows the formulation of (S)-Ibuprofen in suitable topical pharmaceutical dosage forms.

Furthermore, the advantage in using the mixture of ethanol and propylene glycol consists in the possibility to have a large versatility in the preparation of the finished pharmaceutical dosage form which could be, for example, a cream, a gel, a foam or a stick dependently from the used further excipients.

For example, when the finished pharmaceutical dosage form is a cream or a foam, it could contain, in addition to the ethanol:propylene glycol mixture according to the present invention, a suitable solvent, preferably water, a fat phase constituted by one or more lipophilic substances such as waxes, fatty acid esters, cetyl alcohol, stearyl alcohol, fatty acids, triglycerides of fatty acids and one or more anionic, cationic, amphoteric or non-ionic surfactants such as sodium lauryl sulfate, cetyltrimethylammonium bromide, hydrogenated ethoxylated castor oil, ethylene oxide-propylene oxide copolymer, polyoxyethylene-sorbitan monolaurate and alkylamidobetaine.

When the finished pharmaceutical dosage form is a gel, it could contain, in addition to the ethanol:propylene glycol mixture according to the present invention, a suitable amount of one or more gelling substances such as for example carboxypolymethylene, magnesium and aluminum silicates and cellulose ethers and an optional solvent which could be water, when a hydro-alcoholic gel is prepared, or, for example, ethanol itself or polyethylene glycol, when an anhydrous gel is prepared.

When the finished pharmaceutical dosage form is a stick, it could contain, in addition to the ethanol:propylene glycol mixture according to the present invention, a suitable amount of one or more substances such as dibenzylidensorbitol acetal, sodium stearate and solid semisynthetic glycerides able to give a solid consistency to the formulation.

The topical pharmaceutical dosage forms according to the present invention could optionally contain further excipients such as preserving agents like methyl para-hydroxybenzoate, propyl para-hydroxybenzoate, imidazolidinylurea or sodium dehydroacetate, colouring agents, opacifiers, perfumes, buffers, chelating agents and antioxidants.

Some examples of topical pharmaceutical dosage forms according to the present invention are the following.

A) A cream constituted by (weight percentages):

| (S)-Ibuprofen    | 2.5–10%   |
|------------------|-----------|
| ethanol          | 20–30%    |
| propylene glycol | 5–50%     |
| fat substance    | 4–15%     |
| surfactants      | 3.5–10%   |
| preserving agents| 0.01–0.3% |
| water            | 0–60%     | the whole being 100%.

B) A foam constituted by (weight percentages):

| (S)-Ibuprofen    | 2.5–10%   |
|------------------|-----------|
| ethanol          | 20–30%    |
| propylene glycol | 5–50%     |
| surfactants      | 10–40%    |
| preserving agents| 0.01–0.3% |
| water            | 20–60%    | the whole being 100%.

C) A gel constituted by (weight percentages):

| (S)-Ibuprofen    | 2.5–10%   |
|------------------|-----------|
| ethanol          | 20–30%    |
| propylene glycol | 5–50%     |
| further solvent  | 5–40%     |
| gelling agents   | 1–6%      |
| preserving agents| 0.01–0.3% |

D) A stick constituted by (weight percentages):

| (S)-Ibuprofen    | 2.5–10%   |
|------------------|-----------|
| ethanol          | 20–30%    |
| propylene glycol | 5–50%     |
| structuring agent| 2–50%     |
| preserving agents| 0.01–0.3% | the whole being 100%.

From a practical point of view, the preparation of the topical pharmaceutical dosage forms according to the present invention is particularly simple because it consists in mixing the base composition containing the active ingredient, ethanol and propylene glycol with the suitable usual excipients used in pharmaceutical technology in order to obtain the desired finished pharmaceutical dosage form. For example, for the preparation of a cream according to the invention, the base composition will be mixed with an aqueous solution containing the surfactants and the optional further hydrosoluble excipients. The resultant solution will be then mixed with the fat phase in a homogenizer.

The preparation of a foam according to the invention will be carried out by preparing an aqueous solution of a mixture of suitable surfactants and then adding it to the base composition. The distribution of the resultant solution in a container suitable for spray administration will allow to administer the composition object of the invention in the form of a foam at the time of use. The preparation of a stick according to the invention will be carried out in a way similar to that described for the creams but by using the suitable excipients which allow to obtain a solid rather than a semisolid dosage form.

The preparation of a gel according to the invention will be carried out by mixing in a homogenizer an ethanolic solution containing the active ingredient, propylene glycol and the mixture of the remaining excipients.

The finished pharmaceutical dosage forms according to the present invention are also characterized by a remarkable stability as demonstrated by the stability tests carried out for 1 year at room temperature and at 30° C.

In these stability test, no significant decrease of the amount of active ingredient has been observed.

The composition object of the present invention, besides allowing the formulation of (S)-Ibuprofen in topical pharmaceutical dosage forms, shows the further advantage to assure a higher cutaneous permeation of the active ingredient.

In fact, the transdermal crossings of (S)-Ibuprofen obtained after treatment with equal amounts of a composition according to the present invention containing 5% by weight of (S)-Ibuprofen, of a pharmaceutical dosage form on the market containing 10% by weight of Ibuprofen and of a composition according to the already cited European patent application no. 439344 containing 10% by weight of Ibuprofen have been evaluated in vitro. From the obtained data it is clear that, the administered amount of (S)-Ibuprofen being the same, the amount of (S)-Ibuprofen permeated after treatment with the composition object of the present invention is significantly higher (up to 30–40 times) than that absorbed after treatment with the known topical pharmaceutical compositions (Example 9).

This result is particularly surprising since it means that, by using the topical compositions object of the present invention, it is possible to administer a half or even less that a half of the usual therapeutic dose of Ibuprofen in order to achieve the same therapeutic effect of known topical pharmaceutical compositions containing Ibuprofen. In fact, the increased in vitro transdermal crossing obtained with the compositions object of the present invention can be due only in a minimum extent to the known greater permeability and, consequently, activity of (S)-Ibuprofen with respect to Ibuprofen.

In this respect, the literature relating to the topical administration of (S)-Ibuprofen has never described, as far as we know, that the greater activity of (S)-Ibuprofen could consist in practice in halving the doses of the active ingredient or even in decreasing them still more significantly up to 30–40 time less.

Therefore, it can be concluded that the greater transdermal permeation of the compositions object of the present invention is mainly due to the presence of ethanol and propylene glycol in the ratios from 0.6:1 to 4:1 according to the present invention.

The presence of ethanol and propylene glycol in these ratios enables the formulation of (S)-Ibuprofen as well as the optimization of the cutaneous permeation of the active ingredient. This allows also to avoid the use of substances which improve the permeation such as triethanolamine.

In order to better illustrate the present invention, the following examples are now given.

EXAMPLE 1

Preparation of a cream containing 5% (S)-Ibuprofen

A cream having the following composition (weight percentages):

| | |
|---|---|
| (S)-Ibuprofen | 5% |
| ethanol | 20% |
| propylene glycol | 10% |
| polyglycol ester of fatty acids ("Xalifin 15") | 10% |
| cetyl alcohol | 6% |
| ethylene oxide-propylene oxide copolymer ("Lutrol F 127") | 7% |
| water | 42% | was prepared according to the following procedure.

"Lutrol F 127" (trademark of the company BASF) was dissolved in water and the resultant solution was heated at 650° C. (solution A). (S)-Ibuprofen was dissolved in the mixture ethanol-propylene glycol (solution B). The solution B was added to the solution A under stirring and keeping the temperature at 65° C.

Apart, "Xalifin 15" (trademark of the company Vevy) and cetyl alcohol were melted at 70° C. and the melted mass was added to the solution under stirring.

After cooling, the cream was shared into tubes of 15 g each.

EXAMPLE 2

Preparation of a foam containing 5% (S)-Ibuprofen

A foam having the following composition (weight percentages):

| | |
|---|---|
| (S)-Ibuprofen | 5% |
| ethanol | 20% |
| propylene glycol | 10% |
| 30% alkylamido betaine aqueous solution ("Tegobetaina L/7") | 8% |
| 50% sodium lauryl sulfate aqueous solution ("Texapon N40") | 20% |
| water | 37% | was prepared according to the following procedure. (S)-Ibuprofen was dissolved in the mixture ethanol-propylene glycol at room temperature (solution A). "Tegobetaina L/7" (trademark of the company Tego) and "Texapon N40" (trademark of the company Henkel) were dissolved in water at room temperature (solution B). The solution B was slowly poured into solution A and the mixture was kept under slow stirring up to obtaining a clear solution. The solution was shared into containers for spray administration.

EXAMPLE 3

Preparation of a stick containing 5% (S)-Ibuprofen

A stick having the following composition (weight percentages):

| | |
|---|---|
| (S)-Ibuprofen | 5% |
| ethanol | 30% |
| propylene glycol | 46% |
| polyethylene glycol 200 (PEG 200) | 15% |
| dibenzylidenmonosorbitol acetal ("Disorbene LC") | 3.25% |
| hydroxypropylcellulose ("Klucel LF") | 0.75% | was prepared according to the following procedure.

"Disorbene LC" (trademark of the company Roquette) was dissolved in a mixture of propylene glycol and PEG 200 heated at 100° C. (solution A). (S)-Ibuprofen and "Klucel LF" (trademark of the company Aqualon) were dissolved in ethanol and the resultant solution was heated at 60° C. (solution B). The solution B was slowly poured into the solution A by keeping the temperature at 100° C.

The melted mass was shared into sticks and then left to cool spontaneously.

EXAMPLE 4

Preparation of an anhydrous gel containing 5% (S)-Ibuprofen

An anhydrous gel having the following composition (weight percentages):

| | |
|---|---|
| (S)-Ibuprofen | 5% |
| ethanol | 30% |
| propylene glycol | 30% |
| carboxypolymethylene ("Carbopol 1342") | 2.5% |
| polyethylene glycol 300 (PEG 300) | 32.5% | was prepared according to the following procedure.

In a boiler, "Carbopol 13421" (trademark of the company Goodrich) was dispersed into PEG 300 and propylene glycol at room temperature with turbine and maximum vacuum. (S)-Ibuprofen was dissolved in ethanol. The ethanol solution was added to the dispersion and the mixture was homogenized under maximum vacuum. The resultant gel was shared into tubes of 15 g each.

EXAMPLE 5

Preparation of a stick containing 5% (S)-Ibuprofen

A stick having the following composition (weight percentages):

| | |
|---|---|
| (S)-Ibuprofen | 5% |
| ethanol | 30% |
| propylene glycol | 46% |
| polyethylene glycol 200 (PEG 200) | 20% |
| dibenzylidenmonosorbitol acetal ("Disorbene LC") | 3.25% |
| hydroxypropylcellulose ("Klucel LF") | 0.5% | was prepared in a way similar to that described in example 3.

EXAMPLE 6

Preparation of a foam containing 5% (S)-Ibuprofen

A foam having the following composition (weight percentages):

| | |
|---|---|
| (S)-Ibuprofen | 5% |
| ethanol | 20% |
| propylene glycol | 7.5% |
| 30% alkylamido betaine aqueous solution ("Tegobetaine L/7") | 30% |
| hydrogenated and polyethoxylated castor oil ("Cremofor") | 10% |
| water | 27.5% | was prepared in a way similar to that described in example 2.

EXAMPLE 7

Preparation of a cream containing 5% (S)-Ibuprofen

A cream having the following composition (weight percentages):

| | |
|---|---|
| (S)-Ibuprofen | 5% |
| ethanol | 20% |
| propylene glycol | 10% |
| polyglycol ester of fatty acids ("Xalifin 15") | 10% |
| cetyl alcohol | 8% |

| | |
|---|---|
| ethylene oxide-propylene oxide copolymer ("Lutrol F 127") | 5% |
| water | 42% | was prepared in a way similar to that described in example 1.

EXAMPLE 8

Preparation of a cream containing 5% (S)-Ibuprofen

| | |
|---|---|
| (S)-Ibuprofen | 5% |
| ethanol | 20% |
| propylene glycol | 10% |
| polyglycol ester of fatty acids ("Xalifin 15") | 15% |
| cetyl alcohol | 4.5% |
| ethylene oxide-propylene oxide copolymer ("Lutrol F 127") | 3.5% |
| water | 42% | was prepared in a way similar to that described in example 1.

EXAMPLE 9

In vitro transdermal crossings

The topical compositions object of the present invention and some known topical compositions, as a comparison, were evaluated for their ability to cross the skin by using the following procedure. Human skin, obtained from the thoracic-abdominal portion owing to plastic surgery operations, was cleaned from subcutaneous fat with a lancet, cut into disks and freezed at −70° C. At the time of the experiment, the skin was thawed out for about one hour in a buffer (pH 6.8) and put on a Franz cell having the following characteristics:

superficial area: 0.64 cm$^2$ receptor compartment: 4.5 ml thermostatic temperature: 35° C.

The composition to be tested was applied onto the skin in the donor compartment in contact with the horny layer.

Samples of buffer from the acceptor compartment were regularly withdrawn and analyzed in order to determine the Ibuprofen content by using a high pressure liquid chromatograph (HPLC).

As an example, we report the data concerning the transdermal crossings of the composition described in example 6 in comparison with those concerning a composition on the market (Brufen®—cream containing 10% Ibuprofen commercialized by Boots Ltd) and a gel composition containing 10% Ibuprofen prepared as described in the European patent application no. 439344 (Sample 4 on page 9), which will be indicated as Ref. A.

TABLE 1

Data concerning the transdermal crossings of (S)-Ibuprofen or of Ibuprofen for the composition of example 6, Brufen® and Ref. A expressed as amount (μg) permeated from 0 to 6 hours and from 0 to 24 hours.

TABLE 1

Data concerning the transdermal crossings of (S)-Ibuprofen or of Ibuprofen for the composition of example 6, Brufen ® and Ref. A expressed as amount (μg) permeated from 0 to 6 hours and from 0 to 24 hours.

| Composition | Amount permeated from 0 to 6 hours | Amount permeated from 0 to 24 hours |
|---|---|---|
| | (μg/sample ± standard deviation) | |
| Example 6 | 808 ± 359 | 1899.0 ± 267.3 |
| Brufen ® | 66.5 ± 38.7 | 177 ± 95.6 |
| Ref. A | 779.9 ± 100.1 | 2130.6 ± 216 |

From the obtained data, it clearly results that the composition according to the present invention, containing 5% by weight of (S)-Ibuprofen, gives rise to fluxes comparable with those obtained with the reference composition Ref. A, containing 10% by weight of Ibuprofen, while the reference composition Brufen® gives rise to much lower fluxes.

Furthermore, the (S)-Ibuprofen values in the case of the composition of example 6 or of Ibuprofen in the case of Brufen® and of Ref. A were determined as total Ibuprofen and then, in the case of the racemate, the contribution of the (S) enantiomer corresponds to 50%. This means that from a practical point of view, the fluxes produced by a composition according to the present invention are about the double than those produced by the reference composition Ref. A and about 30–40 times higher than those produced by the reference composition Brufen®.

We claim:

1. A cream consisting of by weight:

| | |
|---|---|
| (S)-ibuprofen | 2.5–10% |
| ethanol | 20–30% |
| propylene glycol | 5–50% |
| fat substance | 4–15% |
| one or more surfactants | 3.5–10% |
| one or more preserving agents | 0.1–0.3%; and |
| water | 0–60% | the whole being 100%, the ratio of ethanol to propylene glycol being 0.6:1 to 4:1, said fat substance comprising a lipophilic agent selected from the group consisting of waxes, fatty acid esters, cetyl alcohol, stearyl alcohol, fatty acids, and fatty acid triglycerides.

2. A foam consisting of by weight

| | |
|---|---|
| (S)-Ibuprofen | 2.5–10% |
| ethanol | 20–30% |
| propylene glycol | 5–50% |
| fat substance | 4–15% |
| one or more surfactants | 10–40% |
| one or more preserving agents | 0.1–0.3%; and |
| water | 20–60% | the whole being 100%, the ratio of ethanol to propylene glycol being 0.6:1 to 4:1.

3. A stick consisting of by weight:

| | |
|---|---|
| (S)-Ibuprofen | 2.5–10% |
| ethanol | 20–30% |

-continued

| | |
|---|---|
| propylene glycol | 5–50% |
| structuring agent | 2–50%; and |
| one or more preserving agents | 0.01–0.3% | the whole being 100%, the ratio of ethanol to propylene glycol being 0.6:1 to 4:1, said structuring agent comprising a compound selected from the group consisting of dibenzylidensorbitol acetal, sodium stearate and solid glycerides.

* * * * *